United States Patent [19]

Meilland

[11] Patent Number: Plant 7,276

[45] Date of Patent: Jul. 24, 1990

[54] ROSE PLANT — MEIZOGREL VARIETY

[75] Inventor: Alain A. Meilland, Antibes, France

[73] Assignee: The Conard-Pyle Company, West Grove, Pa.

[21] Appl. No.: 350,117

[22] Filed: May 10, 1989

[51] Int. Cl.[5] ..... A01H 5/00
[52] U.S. Cl. ..... Plt./8
[58] Field of Search ..... Plt. 8

*Primary Examiner*—James R. Feyrer

*Attorney, Agent, or Firm*—Burns, Doane, Swecker & Mathis

[57] ABSTRACT

A new and distinct variety of rose plant of the Miniature Class is provided which forms abundantly and continuously attractive fully-double white blossoms. A compact and bushy growth habit is exhibited. The plant exhibits vigorous vegetation and is well adapted for greenhouse forcing under low light conditions while growing in small containers. A visually appealing flowering pot plant for use as indoor or outdoor decoration is provided.

1 Drawing Sheet

SUMMARY OF THE INVENTION

The new variety of Miniature rose plant was created by artificial pollination wherein two parents were crossed which previously had been studied in the hope that they would contribute the desired characteristics. The female parent (i.e., the seed parent) was the Meiturusa variety (non-patented). The Meiturusa variety is sometimes known as the White Gem variety. The male parent (i.e., the pollen parent) of the new variety was the Cinderella variety (U.S. Plant Pat. No. 1,051). The parentage of the new variety can be summarized as follows:

*Meiturusa* × *Cinderella.*

The seeds resulting from the above pollination were sown and small plantlets were obtained which were physically and biologically different from each other. Selective study resulted in the identification of a single plant of the new variety.

It was found that the new variety of Miniature rose plant of the present invention possesses the following combination of characteristics:

(a) forms in abundance on a continuous basis attractive fully-double white blossoms having firm petals,
(b) forms vigorous vegetation,
(c) exhibits a compact and bushy growth habit, and
(d) is well suited for greenhouse forcing while growing in small containers under low light conditions.

The new variety well meets the needs of the horticultural industry for many usages. It is particularly well-suited for use as attractive ornamentation as a flowering pot plant for use indoors or outdoors.

The new variety has been found to undergo asexual propagation by a number of routes, including budding, grafting, cuttage, etc. The characteristics of the new variety have been found to be strictly transmissible by such asexual propagation from one generation to another.

The new variety has been named the Meizogrel variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were six months of age and were observed during February while growing indoors at LeCannet-de-Maures, Var, France.

DETAILED DESCRIPTION

Figures 1, 2, 3, 4, 5, 6, 7, 8, 9, 10, 11, 12, 13, 14, 15, 16:
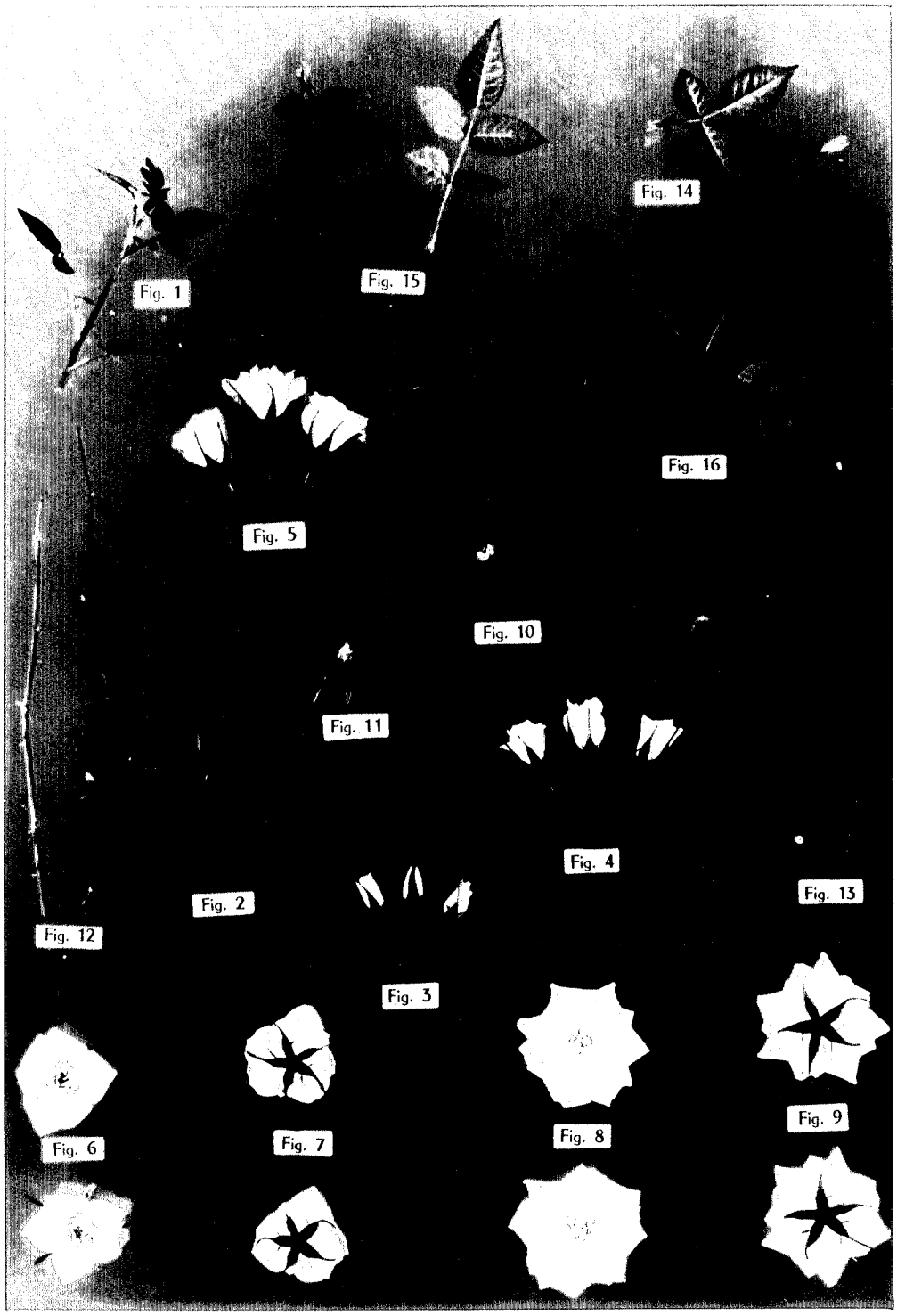
FIG. 1 illustrates a specimen of a young shoot.
FIG. 2 illustrates a specimen of three floral buds before the opening of the sepals.
FIG. 3 illustrates specimens of three floral buds at the opening of the sepals.
FIG. 4 illustrates specimens of three floral buds at the opening of the petals.
FIG. 5 illustrates specimens of three flowers in the course of opening.
FIG. 6 illustrates specimens of two fully open flowers — plan view — obverse.
FIG. 7 illustrates specimens of two fully open flowers — plan view — reverse.
FIG. 8 illustrates specimens of two fully open flowers immediately prior to petal drop — plan view — obverse.
FIG. 9 illustrates specimens of two fully open flowers immediately prior to petal drop — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates specimens of two flowering stems.
FIG. 13 illustrates specimens of two segments of a main branch.
FIG. 14 illustrates specimens of leaves with three leaflets with the under surface being shown on the top of the upper surface being shown on the bottom.
FIG. 15 illustrates specimens of leaves with five leaflets with the upper surface being shown on the left and the under surface being shown on the right.
FIG. 16 illustrates specimens of leaves with seven leaflets with the upper surface being shown on the left and the under surface being shown on the right.

The chart used in the identification of the colors is that of The Royal Horticultural Society (R.H.S. Colour Chart). The terminology which precedes reference to the chart has been added to indicate the corresponding colors in common terms. The description is based on six month old specimens of the new variety during February while growing indoors at LeCannet-de-Maures, Var, France.

Class: Miniature.

Plant:

*Height.*—Approximately 20 cm. on average.

*Habit.*—Bushy.

Branches:

*Color.*—Young stems: light green, Green Group 143B. Adult wood: medium green, Green Group 143A.

*Thorns.*—Size: very small. Quantity: few. Color: pinkish on young stems and greenish on adult wood.

Leaves:

*Petioles.*—Upper surface: striped reddish brown on young foliage and medium green on adult foliage with glandular edges. Under surface: light green with long and very narrow thorns.

*Stipules.*—Adnate, pectinate, narrow and linear.

*Leaflets.*—Number: 3, 5 (most often), and 7. Shape: elliptic. Serration: simple and regular. Texture: firm. General appearance: dense with semi-dull foliage. Color (young foliage): Upper surface: medium green, Green Group 143A. Under surface: light green, Green Group 138B. Color (adult foliage): Upper surface: medium green, Green Group 143A. Under surface: light green, Green group 138B.

Inflorescence:

*Number of flowers.*—Approximately 1 to 5 per stem.

*Peduncle.*—Straight, rigid, light green, smooth, its length is approximately 2 to 3 cm. on average.

*Sepals.*—Upper surface: tormentose, and greenish in coloration. Under surface: light green, smooth, the outside sepals have edges which are slightly appendiculated.

*Buds.*—Shape: conical. Length: approximately 1 to 1.5 cm. on average. Size: small. Color upon opening: Upper surface: white, White Group 155A. Under surface: white, White Group 155A.

*Flower.*—Form: as a flat cup, fully double. Diameter: approximately 4 cm. on average. Color (when opening begins): Upper surface: white, White Group 155A. Under surface: white, White Group 155A. Color (when blooming): Upper surface: white, White Group 155A, commonly with a pinkish heart during the winter. Under surface: white, White Group 155A. Color (at end of opening): Upper surface: white, White Group 155A. Under surface: white, White Group 155A. Fragrance: none. Lasting quality: very long lasting blossoms especially if the plant is grown indoors. Petal number: approximately 18 to 21 on average. Petal form: usually oval, the inner petals are very narrow. Petal texture: firm. Petal drop: good. Anthers: normal, ochre, located at the same height as the stigmas. Stamen number: approximately 35 to 43 on average. Filaments: yellow and of irregular heights. Pistil number: approximately 18 to 21 on average. Stigmas: greenish in coloration. Styles: greenish in coloration, of irregular heights. Receptacle: light green and in longitudinal section it is in the shape of a pitcher.

Development:

*Vegetation.*—Vigorous.

*Blooming.*—Abundant and continuous.

*Resistance to disease.*—Very good.

I claim:

1. A new and distinct variety of Miniature rose plant characterized by the following combination of characteristics:

(a) forms in abundance on a continuous basis attractive fully-double blossoms having firm petals, (b) forms vigorous vegetation, (c) exhibits a compact and bushy growth habit, and (d) is well suited for greenhouse forcing while growing in small containers under low light conditions;

substantially as herein shown and described.

* * * * *